US010035951B2

(12) United States Patent
Lough et al.

(10) Patent No.: US 10,035,951 B2
(45) Date of Patent: Jul. 31, 2018

(54) SECURITY COMPOSITION AND USE THEREOF

(71) Applicant: SmartWater Technology Limited, London (GB)

(72) Inventors: Julie Ann Lough, London (GB); Martin Foord, London (GB); Michael Cleary, London (GB)

(73) Assignee: SmartWater Limited (GB)

( * ) Notice: Subject to any disclaimer, the term of this patent is extended or adjusted under 35 U.S.C. 154(b) by 95 days.

(21) Appl. No.: 14/816,721

(22) Filed: Aug. 3, 2015

(65) Prior Publication Data
US 2016/0032181 A1 Feb. 4, 2016

(51) Int. Cl.
C09K 11/02 (2006.01)
B41M 3/14 (2006.01)
E05B 73/00 (2006.01)
C09D 5/22 (2006.01)
G01N 21/64 (2006.01)

(52) U.S. Cl.
CPC ............. C09K 11/02 (2013.01); B41M 3/144 (2013.01); C09D 5/22 (2013.01); C09K 11/025 (2013.01); E05B 73/0017 (2013.01); G01N 2021/6441 (2013.01)

(58) Field of Classification Search
CPC ........ C09D 5/22; C09K 11/02; C09K 11/025; B41M 3/144; G01N 2021/6441; E05B 73/0017
See application file for complete search history.

(56) References Cited

U.S. PATENT DOCUMENTS

| 3,231,738 | A | * | 1/1966 | Fischer | G01M 3/202 250/302 |
| 5,811,152 | A | * | 9/1998 | Cleary | G09F 3/00 106/31.01 |
| 7,547,894 | B2 | * | 6/2009 | Agrawal | G09F 3/00 250/461.1 |
| 2009/0286250 | A1 | * | 11/2009 | Hayward | C09D 7/1233 435/6.11 |

FOREIGN PATENT DOCUMENTS

| DE | 202010017796 | * 10/2012 |
| GB | 2319337 A | 5/1998 |
| WO | 2013188916 A1 | 12/2013 |
| WO | WO 2013/188916 | * 12/2013 |

OTHER PUBLICATIONS

Translation for DE 202010017796, Oct. 31, 2012.*
Search Report issued in UK Application No. 1413787.1 dated Jan. 28, 2016.

* cited by examiner

Primary Examiner — C Melissa Koslow
(74) Attorney, Agent, or Firm — Forrest Firm, P.C.

(57) ABSTRACT

A security product is disclosed herein comprising a pouch containing a composition, the composition including a mixture of a liquid, a polymer, a light-emitting material and a plurality of marker materials. The pouch may form part of a blocking device blocking an access passage that gives access to a restricted area, such as a manhole, and the composition may be transferred onto an object or individual coming into contact with the composition if an attempt is made to break through the pouch.

13 Claims, 1 Drawing Sheet

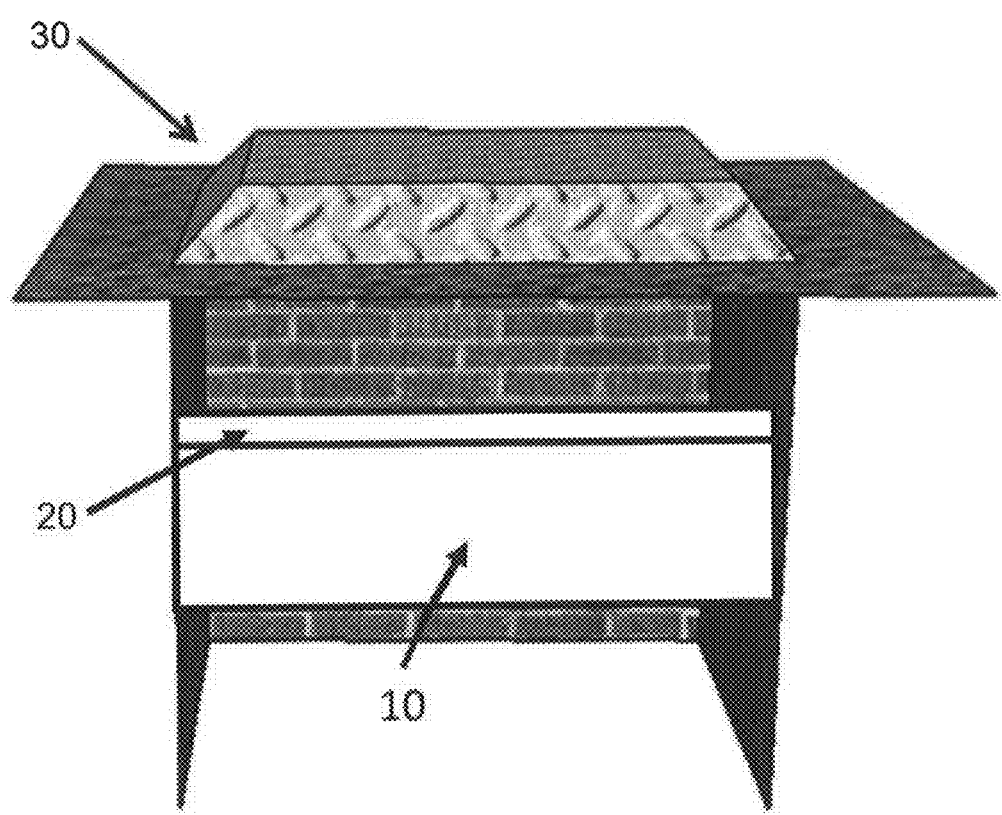

SECURITY COMPOSITION AND USE THEREOF

CROSS-REFERENCE TO RELATED APPLICATIONS

This application is claims priority to Great Britain Patent Application No. 1413787.1 filed Aug. 4, 2014, which is incorporated by reference herein in its entirety for all purposes.

BACKGROUND

Theft is an increasing problem; a recent study has suggested it accounts for almost half of all crimes committed in the UK. This includes unauthorised access to, and theft from, restricted areas. For example, figures released by the British Transport Police reports a 70% increase in metal theft related crime between 2009/10 and 2010/11(Crime in England and Wales 2010/11 Findings from the British Crime Survey and police recorded crime (2nd Edition) Edited by: Rupert Chaplin, John Flatley and Kevin Smith, July 2011 HOSB). In 2011 the cost of metal theft to UK transport and utility companies was estimated at £800 million.

Use of markers to deter or detect theft is known. For example, WO 93/07233 discloses a spray containing a fluorescent material that is used to mark products susceptible to theft, or to spray a thief upon activation of a burglar alarm and WO 2012/175969 discloses application of a unique marker to an electrical cable during manufacture.

One situation in which unauthorised removal of property occurs is intrusion into restricted areas such as street utility boxes or manholes to allow access to underground cables. Under normal circumstances access to these areas are limited and protected by street furniture, manholes or other access points; however coverings can be damaged accidentally by weather, traffic or wear and tear, or may be removed by authorised or unauthorised persons. Once the protective layer is damaged or removed these restricted areas are vulnerable to attack and unauthorised access, for example theft of cables.

It is an object of the disclosure to provide means for preventing or detecting unauthorised entry to restricted areas.

It is a further object of the disclosure to provide means for detection of stolen goods.

SUMMARY OF THE DISCLOSURE

A first aspect the disclosure provides a security product comprising a pouch containing a composition, the composition comprising a mixture of a liquid, a polymer, a light-emitting material and a plurality of marker materials A second aspect the disclosure provides a method of forming plural batches of a marker gel, the method comprising the step of mixing a polymer and a solution comprising a plurality of marker materials wherein the composition of the marker materials in each batch is different.

A third aspect the disclosure provides a gel comprising a light-emitting material and a plurality of marker materials.

A fourth aspect the disclosure provides a marker composition comprising a liquid, at least two different polymers, a light-emitting material and a plurality of marker materials.

The polymers, the marker materials, the liquids and the light-emitting materials of the first, second third and fourth aspects may be as described anywhere herein.

DESCRIPTION OF THE DRAWINGS

Exemplary embodiments of the disclosure will now be described in more detail with reference to the drawings in which:

FIG. 1 illustrates a pouch according to an embodiment of the disclosure used in an access passage with a blocking device for blocking access to the passage.

DETAILED DESCRIPTION

The present disclosure provides a composition for deterring crime, including the theft of property, the unauthorised intrusion into restricted areas and damage or attempted damage to property within or surrounding restricted areas. The present disclosure also provides for identification of goods removed from without authorisation, persons involved in unauthorised entry and/or tooling used in the process of entering premises without authorisation and/or in attempting to enter or to damage premises.

The present disclosure provides a composition, preferably a gel, that is transferrable from one surface to another when wet. Upon drying, the composition may form a film onto the surface it has transferred onto and may merge into the fibres of clothing and/or dry onto hair or skin and so remain in-situ for some extended period of time.

The composition contains one or more polymers and one or more liquid materials and the composition may be a liquid or, preferably, a gel. The composition may have a viscosity of at least about 2000 Pa·s., optionally about 2,000-100,000 Pa·s. or it may be non-Newtonian.

It will be understood by the skilled person that a gel is a semi-solid, or jelly-like, colloidal suspension of a solid, preferably a polymer, dispersed in a liquid.

The composition contains at least one marker material that can be used to identify a location or an object associated with a composition. Preferably, the composition further contains a light-emitting material, preferably a photoluminescent material, to facilitate detection of the composition.

The composition may comprise one or more further materials, for example an adhesive.

Liquid

The liquid of the composition may be a single liquid material or a mixture of liquid materials. The one or more polymers, the one or more light-emitting materials and the one or more markers may be dissolved or dispersed in the liquid.

It will be understood that "liquid material" as used herein is a material that is liquid 20° C., and that the liquid when mixed with other components of the composition may form part of a gel. One or more components of the composition may be dissolved in the liquid.

Suitably, the liquid consists of or comprises water. Exemplary further liquid materials include alcohols, preferably alcohols having a boiling point of less than 100° C., for example propanol and esters, for example glycerol trioleate or isopropyl myristate.

Polymer

The composition contains at least one polymer for forming a viscous composition with the liquid such that the composition transfers readily onto an object or individual corning into contact with the composition. The at least one polymer and the liquid may together form a gel.

If the composition is a gel then the polymer or polymers of the gel may be selected from a wide range of known gel-forming polymers.

The polymer may be selected according to its adhesive properties to facilitate adhesion of the composition onto a surface that the composition is transferred to.

Exemplary polymers for altering the rheology of the composition include cellulose derivatives, acrylic co-polymer derivatives or alkali acrylic emulsions that swell when in contact with water. A preferred class of polymers are anionic acrylates.

The polymer may form 0.1-80 weight % of the composition, optionally 2-70 wt %, optionally 2-20 wt %.

The presence of the polymer may enable formation of a resilient surface coating on a marked object upon transfer drying.

Adhesive

The composition may contain only one polymer for modifying the rheology of the composition, or it may contain one or more further polymers, for example a polymer for improving adhesion of the polymer.

Exemplary polymers with good adhesive properties are polyacrylates and polyacetates and polystyrenes, for example polymethyl methacrylate and polystyrenebutadiene.

The adhesive polymer, where present, is preferably present in a concentration of 0.5-20 weight % of the composition, optionally about 1-10 wt % or about 2-5 wt %.

Marker

The composition comprises one or more marker materials that can be identified using known analytical techniques including, without limitation, spectroscopic and chromatographic techniques, for example mass spectrometry, atomic emission spectroscopy, laser induced breakdown spectroscopy, gas chromatography and gel electrophoresis.

A unique marker composition may be formed by varying parameters including, without limitation, identity of a marker; combination of different marker materials; concentration of an individual marker within the composition; and relative concentrations of two marker materials.

The composition may contain a single marker material, but preferably contains a plurality of different marker materials at least two, at least three, at least four, at least five or at least ten, at least twenty different marker materials. Optionally, the composition comprises up to forty or up to thirty different marker materials. Concentration of marker materials may be measured by ICP-mass spectrometry or ICP atomic emission spectroscopy as a weight per volume of the marker material.

The greater the number of marker materials used, the greater the number of unique combinations available for use. Furthermore, a greater number of marker materials in a composition may provide a greater degree of certainty in identification of the source of the composition.

The concentration of each marker material may be between 0.0000001%-15% (1 ppb-150,000 ppm) for each component, optionally 5-100,000 pm, optionally 100-10,000 ppm. Optionally each marker material is provided in an amount of at least 25 ppm, optionally at least 50 ppm.

A marker composition may be formed as described in UK Patent GB 2413674, the contents of which are incorporated herein by reference. The formulation of unique combinations of marker materials can be prepared using a binary method; however other methods comprising octal and hexadecimal strings can also be used. Each marker composition is held on a database of forensic codes and assigned to a specific owner and/or location. With this database, forensic analysis of a marker composition on an object or on a suspected offender can be used to identify the owner of a marked object or the location at which an offence occurred.

Preferably, the or each marker is an uncommon material provided at a concentration that would not normally be present in the field of use. Exemplary marker materials are metal compounds and organic compounds.

Exemplary metals of metal compound markers include alkaline earth metals, d-block metals, lanthanides, for example Lanthanum, Europium and Holmium; and p-block metals, for example Tellurium and Gallium.

Exemplary organic marker compounds include, tetrahydrocarbazole derivatives and methoxybenzonitrile derivatives.

The or each marker material may be dissolved or dispersed in the composition. Preferably, the or each marker material is dissolved and the metal salt may be selected accordingly. Exemplary metal compound markers include metal oxides, metal triflates, metal halides, metal nitrates, metal sulfates, and metal sulfides.

Light-Emitting Material

The composition preferably contains at least one light-emitting material, preferably a photoluminescent light-emitting material. The or each light-emitting material may independently be fluorescent or phosphorescent. This material can act as a preliminary indicator to indicate the presence of the composition on persons, goods, premises or other property. Upon preliminary identification, the composition may be analysed in detail to identify the markers in the composition.

This indicator can be either overt and/or covert.

Overt indicators emit light in the visible wavelength that can be seen without any apparatus and may be selected from, for example, microdots, pigments and dyes.

Covert indicators can be viewed only with the use of a suitable stimulus, for example photoluminescent materials that only emit visible radiation when excited by radiation other than visible light, for example upon excitation with a UV lamp.

Preferably, the light-emitting material is soluble in the liquid of the composition.

More than one light-emitting material may be present in the composition, for example materials that emit radiation of different wavelengths, for initial identification of the composition.

Exemplary covert indicators are coumarins, oxazinones, stilbenes, fluoresceins and derivatives thereof. Coumarins, oxazinones, stilbenes and derivatives thereof are preferred.

The or each light-emitting material may be used in a concentration of between 0.05 to 40% by weight of the composition.

The pH of such a solution is preferably non-acidic, with a preferred pH value of about 7-12.

Applications

The composition may be placed on or in objects vulnerable to theft, or in areas vulnerable to entry by unauthorised personnel.

The composition may be applied to an object and allowed to dry to form a film. If the object is taken without authorisation (e.g. stolen) then the film may be used to facilitate identification of the owner of the object and/or the location from which it was taken.

The composition may be stored in a pouch. Preferably the pouch is sealed. Preferably the pouch is formed from a flexible material, for example a polymer. The pouch is preferably formed from a low permeability material. Exemplary polymers for forming the pouch are polymers having a density in the range of 300-800 $g/m^2$, for example a 300-800 $g/m^2$ polyethylene.

In use, the pouch may be applied such that it extends across some or all of the area of an access passage that gives access to a restricted area, for example a manhole.

FIG. 1 illustrates a blocking device provided in an access passage such as a manhole to which access is restricted to authorised individuals. In other embodiments, the blocking device may be provided inside a box such as an on-street utility box to prevent unauthorised access to wiring and/or controls within the box.

The blocking device 10 blocks the passage and forms a barrier in addition to, or as an alternative to, manhole cover 30. A pouch 20 containing the formulation as described herein is applied to a surface of the blocking device 10. An individual attempting to gain unauthorised access to the access passage by breaking through the blocking device 10 will break through the pouch 20, causing the composition to be transferred to, and dry on, any tool breaking through the pouch and to any other object or individual coming into contact with the composition.

Following breakage of the pouch 20, the composition will remain readily transferable until the liquid of the composition has evaporated and the composition has dried.

The blocking device 10 may comprise an inflatable bag that conforms to the shape of the access passage upon inflation or deflation using a secure valve, or any other device that is capable of blocking an access passage but that may be vulnerable to removal from the access passage by application of force.

A blocking device 10 in a manhole may also reduce the risk of injury to pedestrians if a manhole cover is not present.

In exemplary embodiments a bag forming a blocking device may include a plurality of distinct air chambers. In some embodiments, the chambers may provide for structural redundancy. Thus, in some embodiments a first chamber may be punctured without the bag loosing structural integrity. The puncture of the first chamber may provide marking. In some embodiments, a shape and/or size of the bag may be selected based on a particular inflation configuration of the bag. Thus, a first bag may be adapted to fit different sized/shaped access points depending on an inflation configuration.

The pouch 20 may be applied to any external surface of the blocking device 10 or, if present, an internal surface of the blocking device, such that the pouch extends across at least part of the access passage. Optionally, the pouch 20 extends across substantially all of the access passage. The pouch may be covered by a layer of the blocking device to prevent removal of the pouch. Optionally, the pouch is provided on an inside surface of a cover of the blocking device.

In another application, the composition as described herein may be applied to a product without use of a pouch to form a film on the product surface. The film may be used to identify the origin and/or owner of the product if it is removed without authorisation.

The present disclosure may be used in conjunction with appropriate signage and warning notices. These warn would be thieves or unauthorised personnel about the presence of the composition and the risk of being marked with the composition should they attempt to steal or damage property, gain unauthorised entry to a restricted area or any other act which may result in damage to property, unauthorised presence in a restricted area or other acts of vandalism or criminality.

Accordingly, the compositions as described herein may be used to deter access to a restricted area or detect unauthorised access to a restricted area, in particular unauthorised access gained by forcefully removing a barrier blocking access to a restricted area.

EXAMPLES

Production of a 1 Liter Volume of Gel:

Triflates of Tellurium, Lanthanum, Gallium, Europium and Holmium were prepared, dissolved in 800 mL deionised water in a concentration of 100 ppm per metal triflate salt and the pH adjusted to 8 pH units using 0.1 M sodium hydroxide. 50 mL of an acrylate based polymer Mowilith LDM 7709 (already suspended in a concentration of 60% in water) was added and the solution 40 mL of BASF Viscalex HV30 rheology modifier was added. The volume of the solution was increased by addition of a further 50 mL of water and the final pH adjusted to 8-9 pH units using 0.1M sodium hydroxide. A fluorescent material (as a 0.7% overall concentration in the solution) and fungicide were added along with more water to bring the volume to 1 Liter. This emulsion was shaken vigorously to produce a thick gel.

Although the apparatus, systems and methods of the disclosure has been described in terms of specific exemplary embodiments, it will be appreciated that various modifications, alterations and/or combinations of features disclosed herein will be apparent to those skilled in the art without departing from the scope of the invention as set forth in the following claims.

What is claimed is:

1. A security product comprising a pouch containing a composition, the composition comprising a mixture of a liquid, a polymer, a light-emitting material and a plurality of marker materials, wherein the polymer is an anionic acrylate copolymer.

2. A security product according to claim 1 wherein the composition is a gel.

3. A security product according to claim 1 wherein the polymer forms 0.1-80 weight % of the composition.

4. A security product according to claim 1 wherein the marker materials are metal compounds.

5. A security product according to claim 4 wherein the metal compounds are selected from alkaline earth metals, d-block metals, lanthanides and p-block metals.

6. A security product according to claim 4 wherein the marker materials include at least one lanthanide compound.

7. A security product according to claim 1 wherein each marker is provided in a concentration in the range of 1 ppb-150,000 ppm.

8. A security product according to claim 1 wherein the composition further comprises an adhesive.

9. A security product according to claim 8 wherein the adhesive is a polymer is selected from polyacrylates, polyacetates and polystyrenes.

10. A security product according to claim 1 wherein the pouch is a flexible material.

11. A security product according to claim 1 wherein the liquid is water.

12. A security product according to claim 1 wherein the light-emitting material emits visible light upon excitation.

13. A method of forming a plurality of gel batches, the method comprising the step of mixing a gel-forming polymer and a solution comprising a plurality of marker materials wherein the composition of the marker materials in each of the gel batches is different, wherein the polymer is an anionic acrylate copolymer.

* * * * *